United States Patent [19]
Owen

[11] Patent Number: 6,014,864
[45] Date of Patent: Jan. 18, 2000

[54] CRYOGENIC FLUID HEAT EXCHANGER METHOD AND APPARATUS

[75] Inventor: Donald R. Owen, New Orleans, La.

[73] Assignee: Life Science Holdings, Inc., Chicago, Ill.

[21] Appl. No.: 09/039,443

[22] Filed: Mar. 16, 1998

[51] Int. Cl.$^7$ .............................. F25B 19/00; F17C 9/02; F25D 11/00

[52] U.S. Cl. ................ 62/51.1; 62/50.2; 62/86; 62/383; 62/437; 165/96

[58] Field of Search ..................... 62/51.1, 50.2, 62/616, 434, 437, 258, 86, 383; 165/96

[56] References Cited

U.S. PATENT DOCUMENTS

| | | | |
|---|---|---|---|
| 2,726,658 | 12/1955 | Chessey | 62/293 |
| 3,018,632 | 1/1962 | Keith | 62/50.2 |
| 3,289,424 | 12/1966 | Shepherd | 62/51.1 |
| 3,369,550 | 2/1968 | Armao | 62/293 |
| 3,385,073 | 5/1968 | Snelling | 62/383 |
| 3,658,066 | 4/1972 | Saidi et al. | 62/293 |
| 3,721,101 | 3/1973 | Sheppard et al. | 62/383 |
| 3,827,251 | 8/1974 | Koski et al. | 62/217 |
| 3,922,878 | 12/1975 | Jalali (Karchay) | 62/384 |
| 3,972,202 | 8/1976 | Stearns | 62/51.1 |
| 5,522,215 | 6/1996 | Matsunaga et al. | 62/383 |
| 5,778,681 | 7/1998 | Li et al. | 62/50.2 |

*Primary Examiner*—William Doerrler
*Attorney, Agent, or Firm*—Oliff & Berridge, PLC

[57] ABSTRACT

A method, and apparatus for implementing the method, utilize cryogenic fluids to cool a fluid. The method includes receiving and allowing expansion of a first compressed cryogenic fluid within a chamber; flowing a second fluid past said chamber; and allowing the transfer of heat between the chamber and the second fluid. The method may further include maintaining the second fluid at a predetermined temperature by controlling the transfer of heat between the chamber and the second fluid. The apparatus includes a chamber for receiving therein and allowing expansion of a compressed cryogenic fluid. The chamber includes at least one wall formed of a material having a high thermal conductivity and high resistivity to low temperature. The chamber may include an insert for receiving cryogenic fluid therein and dispersing the cryogenic fluid through a plurality of holes into the chamber. The apparatus may also include a fluid path component for circulating therethrough the second fluid.

21 Claims, 2 Drawing Sheets

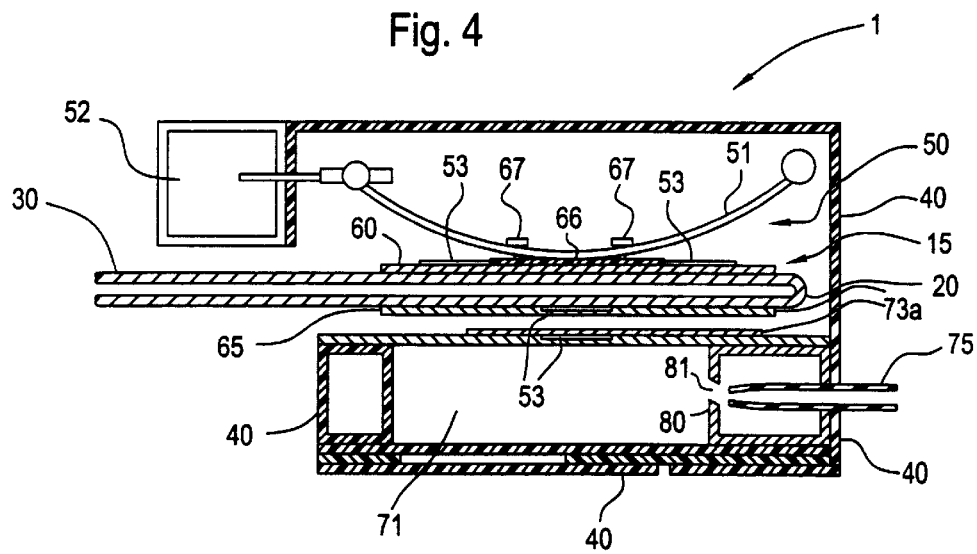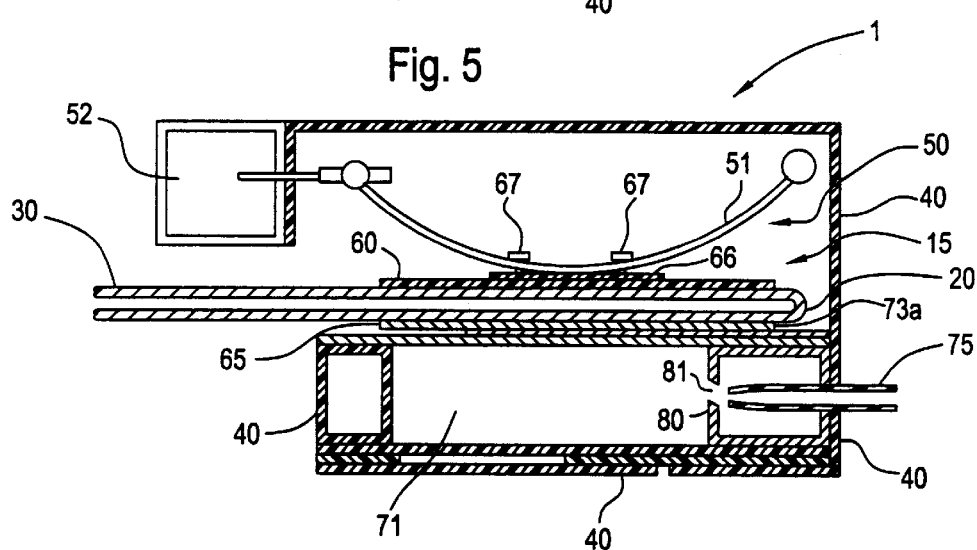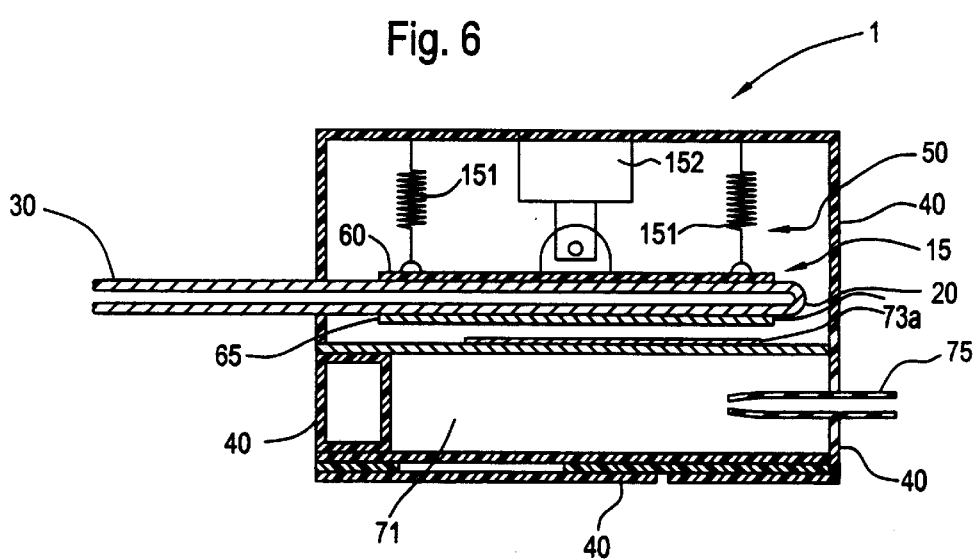

CRYOGENIC FLUID HEAT EXCHANGER METHOD AND APPARATUS

BACKGROUND OF THE INVENTION

1. Field of Invention

The invention relates to a method and apparatus for quickly cooling fluids and maintaining fluids at a low temperature. The apparatus is particularly useful for rapid cooling of medical fluids.

2. Description of Related Art

In the past, there have been various refrigeration devices for cooling and/or storing fluids at a low temperature. Such devices include conventional refrigeration devices and thermoelectric cooling devices.

Conventional refrigeration devices cool utilizing a refrigeration box, expansion valve, compressor and condenser. The expansion valve is where liquid refrigerant expands and changes to cold vapor. The cold vapor absorbs heat and travels to the compressor. The compressor compresses the refrigerant vapor. The condenser discharges absorbed heat into the surrounding ambient, converting the compressed vapor into high pressure liquid refrigerant. Another expansion valve reduces the liquid pressure cooling the liquid refrigerant. The cooled liquid refrigerant is then returned to the first expansion valve and the cycle repeats.

Conventional thermoelectric cooling devices are similar in principle to the conventional refrigeration devices. However, the refrigerant in both liquid and vapor form is replaced by two dissimilar conductors. The surface of the refrigeration box is cooled through adsorption of energy by electrons as they pass from one semiconductor to another. The compressor is replaced by a direct current power source which pumps the electrons from one semiconductor to another. A heat sink replaces the condenser, discharging accumulated heat energy from the system.

However, none of these devices are capable of quickly cooling fluids to a very low temperature and maintaining the fluids at a very low temperature. Such devices are inefficient as they consume large amounts of power to provide cooling and to maintain fluids at a desired temperature ready when needed. Additionally, such devices have complex moving parts, which increase the cost of manufacture and require frequent maintenance.

SUMMARY OF THE INVENTION

The method and apparatus according to the invention are capable of quickly cooling fluids and maintaining fluids at a low temperature. The method and apparatus according to the invention cool fluids utilizing cryogenic fluids. Cryogenic fluids are fluids capable of producing very low temperatures. Cryogenic fluids, such as, for example, carbon dioxide and nitrogen, have very low boiling points. They are capable of absorbing very large amounts of heat to produce very low temperatures in adjacent materials when they change from one state to another, for example, from a liquid or solid state to a gaseous state. In addition, when a compressed cryogenic fluid is allowed to expand, its temperature decreases and the cryogenic fluid is capable of cooling adjacent materials by absorbing heat from the materials as the compressed fluid expands.

The method and apparatus according to the invention utilize the heat transfer ability of such cryogenic fluids to cool other fluids. Further, the method and apparatus according to the invention are capable of maintaining fluids at a low temperature by controlling the heat transfer between the cryogenic fluids and the fluids being cooled. Further, the apparatus is more efficient than conventional refrigeration devices and thermoelectric cooling devices as it is capable of quickly cooling fluids to a low temperature and maintaining the fluids at a low temperature without the need for a constant power supply. Additionally, the apparatus need have no complex moving parts, so it is less expensive to manufacture and requires less maintenance than conventional refrigeration devices and thermoelectric cooling devices. Further, as the apparatus requires less complicated and fewer parts than conventional refrigeration devices and thermoelectric cooling devices, it can be made light weight and highly portable.

BRIEF DESCRIPTION OF THE DRAWINGS

These and other aspects and advantages of the invention will become apparent from the following detailed description of embodiments when taken in conjunction with the accompanying drawings, in which:

FIG. 4 is an example of an alternative cross-sectional configuration of the apparatus of FIG. 1 taken along line IV—IV of FIG. 1;

FIG. 5 is a cross-sectional view of the apparatus of FIG. 4 showing the solenoid actuator actuated; and FIG. 6 is an example of another alternative cross-sectional configuration of the apparatus of FIG. 1 employing an alternative control device.

DETAILED DESCRIPTION OF PREFERRED EMBODIMENTS

Figure 1:
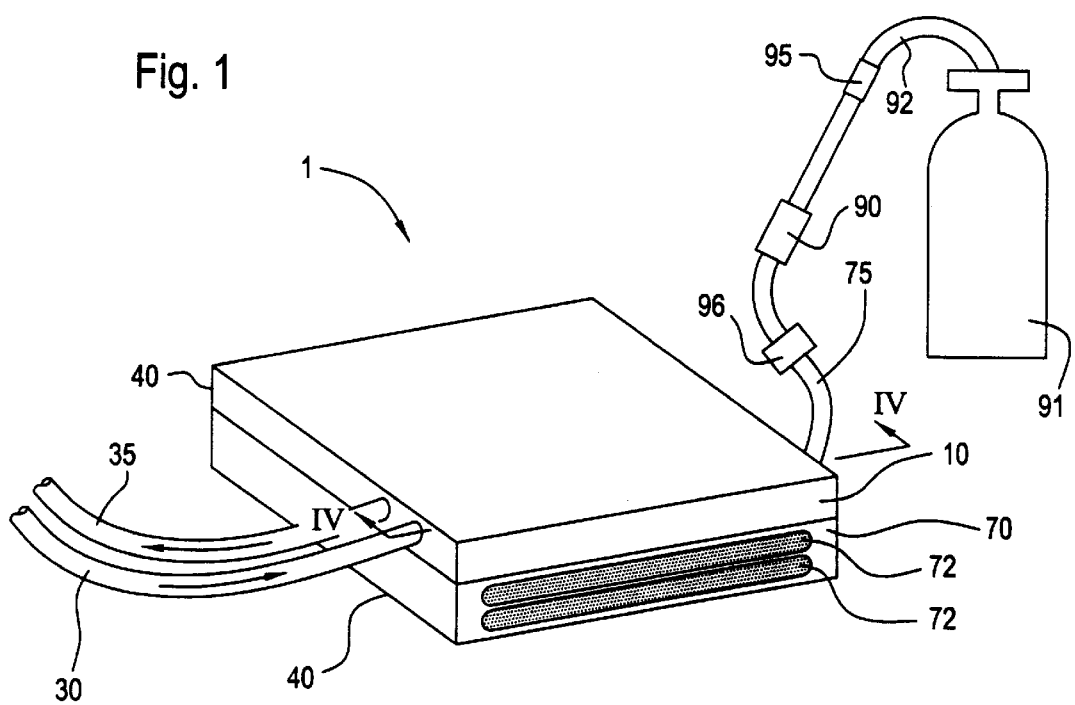
FIG. 1 is a front perspective view of an apparatus according to the invention.
Figure 2:
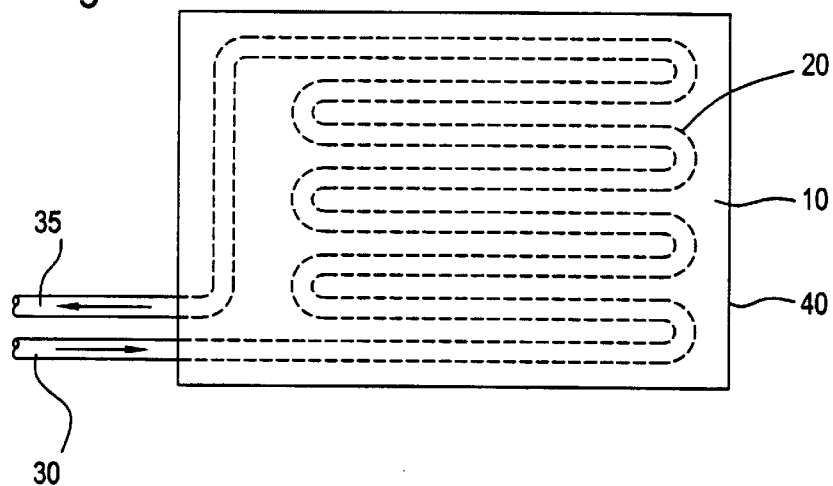
FIG. 2 is a top view of a fluid path component for the apparatus of FIG. 1.
Figure 3:
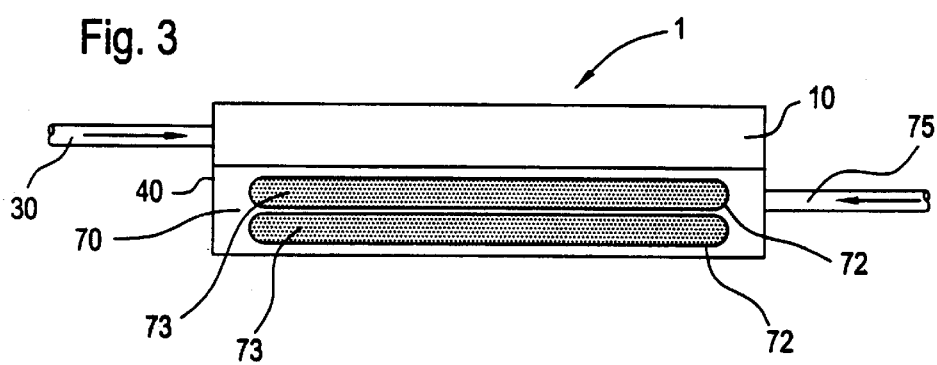
FIG. 3 is a side view of the apparatus of FIG. 1.

For a general understanding of the features of the invention, reference is made to the drawings. In the drawings, like reference numerals have been used throughout to designate like elements.

According to the invention, a method of cooling fluids includes receiving and allowing expansion of a compressed cryogenic fluid within a chamber, flowing a fluid to be cooled, for example, a medical fluid, past the chamber, and allowing the transfer of heat between the chamber and the fluid to be cooled. The method may further include maintaining the fluid at a predetermined temperature by controlling the transfer of heat between the chamber and the fluid to be cooled. Also, the method may include dispersing the cryogenic fluid through a plurality of holes into the chamber.

The transfer of heat may be accomplished by providing the chamber with at least one wall formed of a material having high thermal conductivity and high resistivity to low temperature. The cryogenic fluid may be dispersed and directed through a plurality of holes onto the at least one wall.

As the compressed cryogenic fluid expands in the chamber, its temperature changes. Heat is transferred through the at least one highly thermally conductive wall between the chamber and the fluid to be cooled. By controlling the amount of heat transfer, the fluid to be cooled on the other side of the wall may be maintained at a predetermined temperature. Dispersing the compressed cryogenic fluid through a plurality of holes into the chamber can ensure that a greater surface area of the at least one wall is cooled. Directing the compressed cryogenic fluid through a plurality of holes onto the at least one wall further ensures that a greater surface area of the at least one wall is cooled.

The transfer of heat may be further accomplished by circulating a fluid to be cooled through a fluid path disposed adjacent the at least one wall, preferably on the opposite side of the wall from the cryogenic fluid. Further, the fluid path may be disposed in a fluid path assembly and the fluid may be maintained at a predetermined temperature by selectively moving the fluid path assembly toward (e.g., into contact with) and away from the at least one wall.

The method may also include venting gases produced during expansion from the chamber. Further, the method may include providing the compressed cryogenic fluid from a compressed cryogenic fluid source and utilizing solidified cryogenic fluid within the chamber to continue the transfer of heat between the chamber and the fluid to be cooled after the compressed cryogenic fluid source has been exhausted, turned off or disconnected.

Further, the method may be implemented by apparatus such as that discussed below.

A heat exchanger apparatus of the invention includes a chamber for receiving therein and allowing expansion of a compressed cryogenic fluid. The chamber includes at least one wall formed of a material having a high thermal conductivity and high resistivity to low temperature. The device is configured to permit a fluid to be cooled to flow past the aforesaid wall, for example, in a fluid path component for circulating therethrough the fluid to be cooled. The fluid path component may include an inlet fluid path, an outlet fluid path and a fluid path assembly disposed therein. The fluid path assembly may include a first support plate, a second support plate and a fluid path disposed therebetween. Further, the fluid path may be tortuous.

The chamber may include an insert configured to receive therein the compressed cryogenic fluid and disperse the compressed cryogenic fluid into the chamber. The insert may, for example, be elongated and include holes, slanted so as to direct and disperse the compressed cryogenic fluid onto the highly thermally conductive wall. Further, the chamber may include a vent to release gaseous cryogenic fluid to the atmosphere, which may or may not be a filtered vent. The filter keeps solids in the chamber while letting gases escape. In the case of, for example, carbon dioxide, a block of dry ice may be created within the chamber. The block of dry ice can act as a secondary source of cooling, in particular, when the pressurized cryogenic fluid source is no longer operatively connected to the chamber.

The apparatus may further include a control device for forcing, upon actuation of the control device, the fluid path assembly toward (e.g., against) the chamber wall to cool the fluid circulating through the fluid path component. The control device may include one or more springs or other structure for biasing the fluid path assembly toward or away from the chamber. The spring or springs may be attached to the fluid path assembly and to an actuator or to an outer casing of the apparatus.

Further, the apparatus may include temperature sensors in communication with the control device. The temperature sensors may provide signals to the control device so that the control device may move the fluid path assembly in response to the sensed temperature and/or alarms. Additionally, the fluid path component and the chamber may be housed together in an outer casing formed of a material having low thermal conductivity and high resistivity to low temperature.

Preferred embodiments for implementing the method of the invention are discussed below with reference to the drawings.

As shown in FIG. 1, the apparatus 1 is a heat exchanger apparatus that allows a compressed cryogenic fluid source, for example, a liquid nitrogen, liquid carbon dioxide or similar source, to be used to produce a controlled temperature drop as fluid to be cooled flows into and through the apparatus.

The apparatus 1 includes a fluid path component 10 and a cryogenic fluid cooling component 70. The fluid path component 10 and the cryogenic fluid cooling component 70 are both housed in a casing 40, which is preferably formed of a material having a low thermal conductivity and high resistivity to low temperature, such as, for example, plastic, plastic composite, wood, carbon epoxy resin.

The fluid path component 10 includes a fluid inlet path 30, a fluid outlet path 35 and a fluid path assembly 15 disposed therein. The fluid path assembly 15 includes a fluid path 20 supported by first and second support plates 60, 65. The first support plate 60 is preferably formed of a material having a low thermal conductivity and high resistivity to low temperature, such as, for example, plastic, plastic composite, wood, carbon epoxy resin. The second support plate 65 is preferably formed of a material having a high thermal conductivity and high resistivity to low temperature, such as, for example, metals such as aluminum, aluminum oxide composite, stainless steel. The fluid path 20 is preferably tortuous in shape. A tortuous fluid path provides a greater surface area for cooling than, for example, a straight fluid path. The fluid path is preferably 3 to 6 feet in length and formed of a material having a high thermal conductivity and high resistivity to low temperature, such as, for example, metals such as aluminum, aluminum oxide composite, stainless steel. The fluid path can be a separate tube disposed between the support plates or may be formed by walls connecting the support plates. Further, the fluid path may be disposable Referring to FIG. 4, the cryogenic fluid cooling component 70 includes a cryogenic fluid cooling chamber 71. The cryogenic fluid cooling chamber 71 includes an inner wall 73 preferably formed of a material having a high thermal conductivity and high resistivity to low temperature, such as, for example, metals such as aluminum, aluminum oxide composite, stainless steel. An additional support plate 73a may also be provided. The chamber 71 may also include an insert 80 configured to receive cryogenic fluid from a pressurized cryogenic fluid tank 91 via a cryogenic fluid inlet path 75 and disperse the cryogenic fluid. The insert 80 may include holes 81 configured to direct and disperse cryogenic fluid within the cryogenic fluid cooling chamber 71. The holes 81 are preferably slanted to direct cryogenic fluid onto the inner wall 73 to facilitate heat transfer from the chamber 71 to the fluid path component 10. However, the insert 80 can be eliminated and the cryogenic fluid introduced directly into the chamber 71, as shown in FIG. 6.

The cryogenic fluid inlet path 75 is connected to a cryogenic fluid tank outlet path 92 by means of a cryogenic fluid conduit coupling device 90. The coupling device 90 preferably provides easy coupling of two fluid conduits at very low temperatures without creating a pressure change across the coupling. An example of a cryogenic fluid conduit coupling device is discussed in detail in simultaneously filed co-pending application Ser. No. 09/039,378, which is hereby incorporated by reference. Alternatively, the coupling device 90 may be incorporated into the cryogenic fluid cooling component 70. Pressure relief valves 95, 96 are provided on each of the cryogenic fluid inlet path 75 and the cryogenic fluid tank outlet path 92 to prevent pressure buildup.

The cryogenic fluid is received into the insert 80 and is dispersed into the chamber 71, through holes 81. In the case of use of liquefied carbon dioxide as the cryogenic fluid, $CO_2$ snow may be formed due to the pressure drop. The chamber 71 may be provided with one or more vents 72, which may be filtered to allow only gases to escape. For example, in the case of carbon dioxide, the filter holds in the $CO_2$ snow while letting gases produced escape. This allows a block of dry ice to form within the chamber. The block of dry ice acts as a secondary source of cooling, in particular, when the pressurized cryogenic fluid source is exhausted.

The fluid path assembly 15 can be moved toward or against and moved away from the chamber 71 by means of a control device 50 to control the amount of heat exchange between the chamber 71 and the fluid within the fluid path 20. Temperature sensors 53 may be provided on a surface of the inner wall 73 and on one or both of the first and second supports 61, 65, or elsewhere. The apparatus 1 may by controlled by a microprocessor based on the initial fluid temperature, ambient temperature, desired fluid temperature and desired flow rate. A shunt (not shown) and heater circuit (not shown) may be present in case of sensor or control failure on the support plate 60 or wall 73 to re-heat the fluid.

The control device 50 may include a spring, for example, an arcuate carbon spring 51, as shown in FIG. 4, attached via screws 67, 67 and a connector plate 66 to the first support plate 60. Upon actuation of an actuator, for example, a solenoid actuator 52, the spring 51 is flexed to force the fluid path assembly 15 against the cryogenic fluid cooling component 70. Upon deactuation of the solenoid actuator 52, the fluid path assembly 15 is allowed to move away from the cryogenic fluid cooling component 70. FIG. 6 shows an alternative control device 150. This device includes a pneumatic or hydraulic actuator 152 and two springs 151, 151 connected between the first support plate 62 and the outer casing 40, but functions similarly to the device of FIGS. 4 and 5. With two-way positive control of the actuator, the spring or springs may be eliminated. Other guiding structure may be included if desired.

Now the operation of the apparatus will be described below.

In operation, fluid is circulated through the fluid path 20 via fluid inlet path 30 and outlet path 30. Then, a valve on the pressurized cryogenic fluid tank 91 is opened to start the flow of cryogenic fluid. The cryogenic fluid flows through the cryogenic tank fluid outlet path 92 and the cryogenic fluid inlet path 75. The cryogenic tank fluid outlet path 92 and the cryogenic fluid inlet path 75 are connected by the cryogenic fluid conduit coupling device 90 and are preferably formed of flexible material having excellent properties against high pressure and low temperature, such as, for example, rubber, polyphosphine tubing, corrugated polytetrafluoroethylene, aluminum coated with a hydrophilic urethane coating. The cryogenic fluid flows into the chamber 71, via the insert 80, if provided. The cryogenic fluid is then ejected through holes 81 into the chamber 71. Alternatively, the cryogenic fluid may be introduced directly into the chamber 71. During injection into the chamber 71, the cryogenic fluid expands and its temperature drops. Cryogenic fluid such as liquefied carbon dioxide, when pressure is reduced, may form a mixture of "snow", or solidified carbon dioxide, and gaseous carbon dioxide. Gases can exit the apparatus via vents 72. The "snow" builds up within the chamber 71 and provides secondary cooling, in particular, when the cryogenic fluid source is exhausted or turned off.

Upon actuation of the control device 50, 150, the fluid path assembly 15 is pressed against the cryogenic fluid cooling component 70 to allow heat transfer and cooling of the fluid circulating through the fluid path 20. The temperature sensors 53 sense the temperature being produced at the chamber 71 and on the first and second support plates 60, 65. The sensed temperatures are provided to the microprocessor (not shown) which controls the heat exchange between the chamber 71 and the fluid by controlling the control device 50, 150, moving the fluid path assembly 15 away from the chamber 71 should the temperature fall below a predetermined parameter, and then returning the fluid path assembly 15 to its position adjacent the chamber 71. Preferably the inner wall 73 is maintained at a temperature of approximately 1 to 5° C.

While the invention has been described in conjunction with a specific embodiment thereof, it is evident that many alternatives, modifications and variations may be apparent to those skilled in the art. Accordingly, the preferred embodiment of the invention as set forth herein is intended to be illustrative, not limiting. Various changes may be made without departing from the spirit and scope of the invention as defined in the following claims.

What is claimed is:

1. A method of cooling a medical fluid, comprising:
   receiving and allowing expansion of a compressed cryogenic fluid within a chamber;
   flowing a medical fluid through a fluid flow path apparatus disposed adjacent to said chamber so that the medical fluid flows past said chamber;
   allowing the transfer of heat between the chamber and the medical fluid within the fluid flow path apparatus; and
   maintaining the medical fluid at a predetermined temperature by controlling the distance between the chamber and the fluid flow path apparatus.

2. A method of cooling a medical fluid, comprising:
   receiving and allowing expansion of a compressed cryogenic fluid within a chamber by dispersing and directing the cryogenic fluid through a plurality of holes onto at least one thermally conductive wall separating the chamber and the medical fluid, the chamber having a cross-sectional area greater than a collective cross-sectional area of the plurality of holes;
   flowing a medical fluid through a fluid flow path apparatus having a tortuous, planar fluid flow path disposed adjacent to said at least one thermally conductive wall of said chamber; and
   allowing the transfer of heat between the chamber and the medical fluid within the fluid flow path apparatus.

3. The method of claim 1, wherein the chamber has at least one thermally conductive wall separating the chamber and the medical fluid; the method further comprises circulating the medical fluid through a fluid flow path disposed adjacent the at least one wall; the fluid flow path being disposed in a fluid path assembly; and the medical fluid being maintained at the predetermined temperature by selectively moving the fluid flow path assembly into contact with and away from the at least one wall.

4. A method of cooling a medical fluid, comprising:
   receiving and allowing expansion of a compressed cryogenic fluid within a chamber, the chamber having a cross-sectional area greater than a cross-sectional area of a passage through which the compressed cryogenic fluid enters the chamber;
   flowing a medical fluid through a fluid flow path apparatus disposed adjacent to said chamber so that the medical fluid flows past said chamber; and allowing the transfer of heat between the chamber and the medical fluid within the fluid flow path apparatus, wherein the compressed cryogenic fluid is provided from a compressed cryogenic fluid source and the method further comprises utilizing solidified cryogenic fluid within the chamber to continue the transfer of heat between the chamber and the medical fluid.

5. A method of cooling a fluid, comprising:

receiving and allowing expansion of a first compressed cryogenic fluid within a chamber, the chamber having at least one wall;

venting gases produced during expansion from the chamber;

flowing a second fluid through an enclosed fluid flow path having at least one wall disposed adjacent to and in heat exchange communication with said at least one wall of said chamber; and allowing the transfer of heat between the chamber and the second fluid within the enclosed fluid flow path.

6. A method of cooling a fluid, comprising:

receiving and allowing expansion of a first compressed cryogenic fluid within a chamber, the first compressed cryogenic fluid being provided from a compressed cryogenic fluid source;

flowing a second fluid through an enclosed fluid flow path disposed adjacent to said chamber so that the second fluid flows past said chamber;

allowing the transfer of heat between the chamber and the second fluid within the enclosed fluid flow path; and utilizing solidified cryogenic fluid within the chamber to continue the transfer of heat between the chamber and the second fluid after the provision of compressed cryogenic fluid has been stopped.

7. A heat exchanger apparatus, comprising:

a chamber for receiving and allowing expansion therein of a first fluid, the chamber including at least one wall formed of a material having a high thermal conductivity and high resistivity to low temperature; and a fluid flow path component disposed adjacent to said chamber for circulating therethrough a second fluid so that the second fluid flows past said at least one wall of said chamber, the fluid flow path component including an enclosed fluid flow path assembly comprising an inlet fluid flow path, an outlet fluid flow path, a heat exchange fluid flow path disposed therein, and at least one wall disposed adjacent to and in heat communication with said at least one wall of said chamber.

8. The apparatus of claim 7, wherein said fluid flow path assembly comprises a first support plate, said at least one wall of said fluid flow path assembly comprises a second support plate and said heat exchange fluid flow path is disposed between said first and second support plates.

9. A heat exchanger apparatus, comprising:

a chamber for receiving and allowing expansion therein of a first fluid, the chamber including at least one wall formed of a material having a high thermal conductivity and high resistivity to low temperature; and a fluid flow path component adjacent said chamber for circulating therethrough a second fluid, the fluid flow path component including a fluid flow path assembly comprising an inlet fluid flow path, an outlet fluid flow path and a heat exchange fluid flow path disposed therein, wherein the fluid flow path assembly is planar and further comprises a first support plate, a second support plate and said heat exchange fluid flow path disposed therebetween, the heat exchange fluid flow path being tortuous.

10. A heat exchanger apparatus, comprising:

a chamber for receiving and allowing expansion therein of a first fluid, the chamber including at least one wall formed of a material having a high thermal conductivity and high resistivity to low temperature; and a fluid flow path component adjacent said chamber for circulating therethrough a second fluid, the fluid flow path component including a fluid flow path assembly comprising an inlet fluid flow path, an outlet fluid flow path and a heat exchange fluid flow path disposed therein, wherein the fluid flow path assembly is planar and further comprises a first support plate, a second support plate and said heat exchange fluid flow path disposed therebetween, the first support plate being formed of a material having a low thermal conductivity and high resistivity to low temperature and the second support plate being formed of a material having a high thermal conductivity and high resistivity to low temperature.

11. The apparatus of claim 10, wherein the fluid flow path assembly is disposable.

12. The apparatus of claim 7, further comprising a control device for forcing, upon actuation of the control device, the fluid flow path assembly against said wall of the chamber to cool the second fluid circulating through the fluid flow path component.

13. The apparatus of claim 12, wherein the control device comprises at least one spring and an actuator.

14. The apparatus of claim 13, wherein the spring comprises an arcuate spring operably connected to the fluid flow path assembly.

15. The apparatus of claim 13, wherein the at least one spring comprises a pair of springs attached between the first support plate and an outer casing of the apparatus.

16. The apparatus of claim 13, wherein the actuator comprises at least one of a solenoid, a pneumatic actuator and a hydraulic actuator.

17. The apparatus of claim 12, further comprising at least one temperature sensor in communication with the control device.

18. The apparatus of claim 3, wherein the fluid flow path component and the chamber are housed in an outer casing formed of a material having a low thermal conductivity and high resistivity to low temperature.

19. The apparatus of claim 7, wherein the chamber has at least one vent which is filtered to allow gases to escape while retaining solids within the chamber.

20. A cryogenic heat exchanger apparatus, comprising:

a chamber for receiving and allowing expansion therein of a first fluid, the chamber including an insert configured to receive and disperse the first fluid through a plurality of holes into the chamber and at least one wall formed of a material having a high thermal conductivity and high resistivity to low temperature; and a fluid flow path component adjacent said chamber for circulating therethrough a second fluid so that the second fluid flows past said at least one wall of said chamber, the fluid flow path component including an enclosed fluid flow path assembly comprising an inlet fluid flow path, an outlet fluid flow path, a heat exchange fluid flow path, and at least one wall disposed adjacent to and in heat communication with said at least one wall of said chamber.

21. The method of claim 1, wherein the fluid flow path apparatus is formed separate from said chamber and is removed and discarded after use.

* * * * *